US012721920B2

(12) United States Patent
Ma

(10) Patent No.: US 12,721,920 B2
(45) Date of Patent: Sep. 1, 2026

(54) ULTRAVIOLET DISINFECTION PROBE FOR INDWELLING CATHETERS

(71) Applicant: Becton, Dickinson and Company, Franklin Lakes, NJ (US)

(72) Inventor: Yiping Ma, Layton, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 320 days.

(21) Appl. No.: 18/236,767

(22) Filed: Aug. 22, 2023

(65) Prior Publication Data

US 2024/0066168 A1 Feb. 29, 2024

Related U.S. Application Data

(60) Provisional application No. 63/400,241, filed on Aug. 23, 2022.

(51) Int. Cl.

| | |
|---|---|
| ***A61L 2/26*** | (2006.01) |
| ***A61L 2/10*** | (2026.01) |
| ***A61L 103/15*** | (2026.01) |
| ***A61M 25/00*** | (2006.01) |
| ***A61M 39/02*** | (2006.01) |

(52) U.S. Cl.

CPC *A61L 2/26* (2013.01); *A61L 2/10* (2013.01); *A61M 25/0097* (2013.01); *A61M 39/0247* (2013.01); *A61L 2103/15* (2026.01); *A61L 2202/11* (2013.01); *A61M 2025/0019* (2013.01); *A61M 2039/0202* (2013.01); *A61M 2039/0258* (2013.01); *A61M 2039/0285* (2013.01)

(58) Field of Classification Search

CPC ........ A61L 2/10; A61L 2/26; A61M 39/0247; A61M 25/0097

See application file for complete search history.

(56) References Cited

U.S. PATENT DOCUMENTS

| | | | |
|---|---|---|---|
| 10,279,058 | B2 | 5/2019 | Lin et al. |
| 2008/0159908 | A1 | 7/2008 | Redmond |
| 2016/0213945 | A1 | 7/2016 | Burwell et al. |
| 2018/0104368 | A1 | 4/2018 | Dobrinsky et al. |
| 2019/0192814 | A1 | 6/2019 | Tang et al. |
| 2020/0016374 | A1 | 1/2020 | Burkholz et al. |
| 2021/0154450 | A1 | 5/2021 | Matlock et al. |

FOREIGN PATENT DOCUMENTS

| | | | |
|---|---|---|---|
| WO | WO2020014149 | A1 | 1/2020 |
| WO | 2021028595 | A1 | 2/2021 |

*Primary Examiner* — Sean E Conley
(74) *Attorney, Agent, or Firm* — The Webb Law Firm

(57) ABSTRACT

Provided herein is a catheter system that includes an intravenous catheter assembly including a catheter defining a lumen extending between a distal end and a proximal end of the catheter and an access connector configured to provide access to the lumen of the catheter. The catheter system also includes a disinfecting probe coupleable to the access connector, with the disinfecting probe including a housing having a proximal end and a distal end, a lighting system disposed at least partially within the housing and configured to emit a disinfecting ultraviolet light, and an advancement member configured to advance a portion of the lighting system beyond the distal end of the housing and into the catheter, responsive to movement of the advancement member with respect to the housing, wherein the disinfecting ultraviolet light disinfects the lumen of the catheter upon being advanced therein by the advancement member.

21 Claims, 11 Drawing Sheets

108
104
106
70
72,74
66
100b
68
100a
94
96
92

102
101
72,74
82
62
60
76
90
90
86
88
64

72
74
76
72

74
72
74
75
72
75
75
76

108
104
106
112
114

68
78
96
62
110
98
80
90
86
88
64

108
104
106
114
112
100b
68
100a
94
92
102
101
114
110
62
124
90
90
86
88
64

106
104
68
92
78
82
62
101
114
80
110
64
88

106
110
104
78
62
82
101
114
68
92
80
64
88
114
120
124

70
62
132
72,74
136
136b
136a
138
80
72,74
76
88

ULTRAVIOLET DISINFECTION PROBE FOR INDWELLING CATHETERS

CROSS-REFERENCE TO RELATED APPLICATION

The present application claims priority to U.S. Provisional Application Ser. No. 63/400,241, entitled "Ultraviolet Disinfection Probe for Indwelling Catheters", filed Aug. 23, 2022, the entire disclosure of which is hereby incorporated by reference in its entirety.

BACKGROUND OF THE INVENTION

Field of the Invention

Provided herein are devices and systems for use in vascular access, and, in particular, devices and systems for use with blood draw through indwelling catheters.

Description of Related Art

A vascular access device (VAD) may access peripheral vasculature of a patient. A VAD may be indwelling for short term (days), moderate term (weeks), or long term (months to years). VADs may be used for infusion therapy and/or for blood withdrawal.

Common types of VAD include over-the-needle peripheral intravenous catheters (PIVCs), peripherally inserted central catheters (PICCs), central venous catheters (CVCs), and midline catheters. Currently, there may be several limitations to the use of such VADs for fluid infusion or blood draw, including the introduction of instruments for blood withdrawal through the VAD, which can lead to introduction of microbes and catheter-related blood stream infections (CRBSIs).

In some existing VADs, antimicrobial barrier caps are employed to reduce the occurrence of CRBSIs. These barrier caps are cleaning devices designed to keep the catheter hub/connector of the VAD clean, such as by encapsulating a needleless luer valve in an antimicrobial solution. However, while barrier caps are often effective in sanitizing the catheter hub, they do not address the concern of bacteria entering into the fluid path (catheter) of the VAD outside/downstream of the catheter hub. Accordingly, there is a need in the art for devices and systems that provide for disinfection of multiple components of a VAD, including the fluid path outside the catheter hub, to reduce the risk for CRBSIs when introducing instruments into the VAD for performing a blood withdrawal.

SUMMARY OF THE INVENTION

Provided herein is a catheter system that includes an intravenous catheter assembly including a catheter with a distal end and a proximal end and defining a lumen extending between the distal end and the proximal end, and an access connector configured to provide access to the lumen of the catheter. The catheter system also includes a disinfecting probe coupleable to the access connector, with the disinfecting probe including a housing having a proximal end and a distal end, a lighting system disposed at least partially within the housing and configured to emit a disinfecting ultraviolet light, and an advancement member configured to advance a portion of the lighting system beyond the distal end of the housing and into the catheter, responsive to movement of the advancement member with respect to the housing, wherein the disinfecting ultraviolet light disinfects the lumen of the catheter upon being advanced therein by the advancement member.

In some embodiments, the access connector includes a needleless access connector and the disinfecting probe includes a blunt cannula at the distal end of the housing that is reversibly coupleable to the needleless access connector. The advancement member is configured to advance the portion of the lighting system through the blunt cannula and the needleless access connector, into the lumen of the catheter.

In some embodiments, the lighting system includes an ultraviolet light source positioned adjacent the proximal end of the housing and configured to emit the disinfecting ultraviolet light and an optical fiber extending out distally from the ultraviolet light source and configured to transmit the disinfecting ultraviolet light along a length of the optical fiber; wherein the advancement member is configured to advance a portion of the optical fiber beyond the distal end of the housing.

In some embodiments, the lighting system comprises a cladding covering a portion of the optical fiber and that is configured to block transmission of the disinfecting ultraviolet light.

In some embodiments, the cladding covers a full length of the optical fiber except for a tip at a distal end of the optical fiber, such that the disinfecting ultraviolet light is emitted only from the tip.

In some embodiments, wherein the cladding covers a length of the optical fiber and includes openings formed therein at locations spaced apart along the length of the optical fiber, such that the disinfecting ultraviolet light is emitted from the optical fiber only at the locations.

In some embodiments, the lighting system includes a guide wire and a light strip mounted on the guide wire, the light strip having a plurality of ultraviolet light emitting diodes (LEDs) configured to emit the disinfecting ultraviolet light. The advancement member is configured to advance a portion of the guide wire and the light strip beyond the distal end of the housing.

In some embodiments, the plurality of ultraviolet LEDs are equally spaced along a length of the light strip In some embodiments, the advancement member is configured to move along an outer surface of the housing, with the advancement member engaging the lighting system to advance the portion of the lighting system beyond the distal end of the housing and into the catheter.

In some embodiments, the lighting system includes a control system configured to selectively control emission of the disinfecting ultraviolet light, the control system having one or more of an on/off switch, a timer, and a communication device.

In some embodiments, the lighting system is configured to emit UV-C light.

Also provided herein is a disinfecting probe for disinfecting a catheter of an intravenous catheter assembly. The disinfecting probe includes a housing having a proximal end and a distal end, a lighting system disposed at least partially within the housing and configured to emit a disinfecting ultraviolet light, and an advancement member configured to advance a portion of the lighting system beyond the distal end of the housing and into the catheter responsive to movement of the advancement member with respect to the housing, wherein the disinfecting ultraviolet light disinfects a lumen of the catheter upon being advanced therein by the advancement member.

In some embodiments, the disinfecting probe further includes a blunt cannula positioned at the distal end of the housing that is reversibly coupleable to a needleless access connector of the intravenous catheter assembly, with the advancement member configured to advance the portion of the lighting system through the blunt cannula and the needleless access connector, into the lumen of the catheter.

In some embodiments, the lighting system includes an ultraviolet light source positioned adjacent the proximal end of the housing and configured to emit the disinfecting ultraviolet light and an optical fiber extending out distally from the ultraviolet light source and configured to transmit the disinfecting ultraviolet light along a length of the optical fiber. The advancement member is configured to advance a portion of the optical fiber beyond the distal end of the housing.

In some embodiments, the lighting system includes a cladding covering a portion of the optical fiber that is configured to block transmission of the disinfecting ultraviolet light.

In some embodiments, the cladding covers a full length of the optical fiber except for a tip at a distal end of the optical fiber, such that the disinfecting ultraviolet light is emitted only from the tip.

In some embodiments, the cladding covers a length of the optical fiber and includes openings formed therein at locations spaced apart along the length of the optical fiber, such that the disinfecting ultraviolet light is emitted from the optical fiber only at the opening locations.

In some embodiments, the lighting system includes a guide wire and a light strip mounted on the guide wire, the light strip having a plurality of ultraviolet light emitting diodes (LEDs) configured to emit the disinfecting ultraviolet light. The advancement member is configured to advance a portion of the guide wire and the light strip beyond the distal end of the housing.

In some embodiments, the plurality of ultraviolet LEDs are equally spaced along a length of the light strip.

In some embodiments, the advancement member is configured to move along an outer surface of the housing, with the advancement member engaging the lighting system to advance the portion of the lighting system beyond the distal end of the housing and into the catheter.

DESCRIPTION OF THE INVENTION

Figure 1:
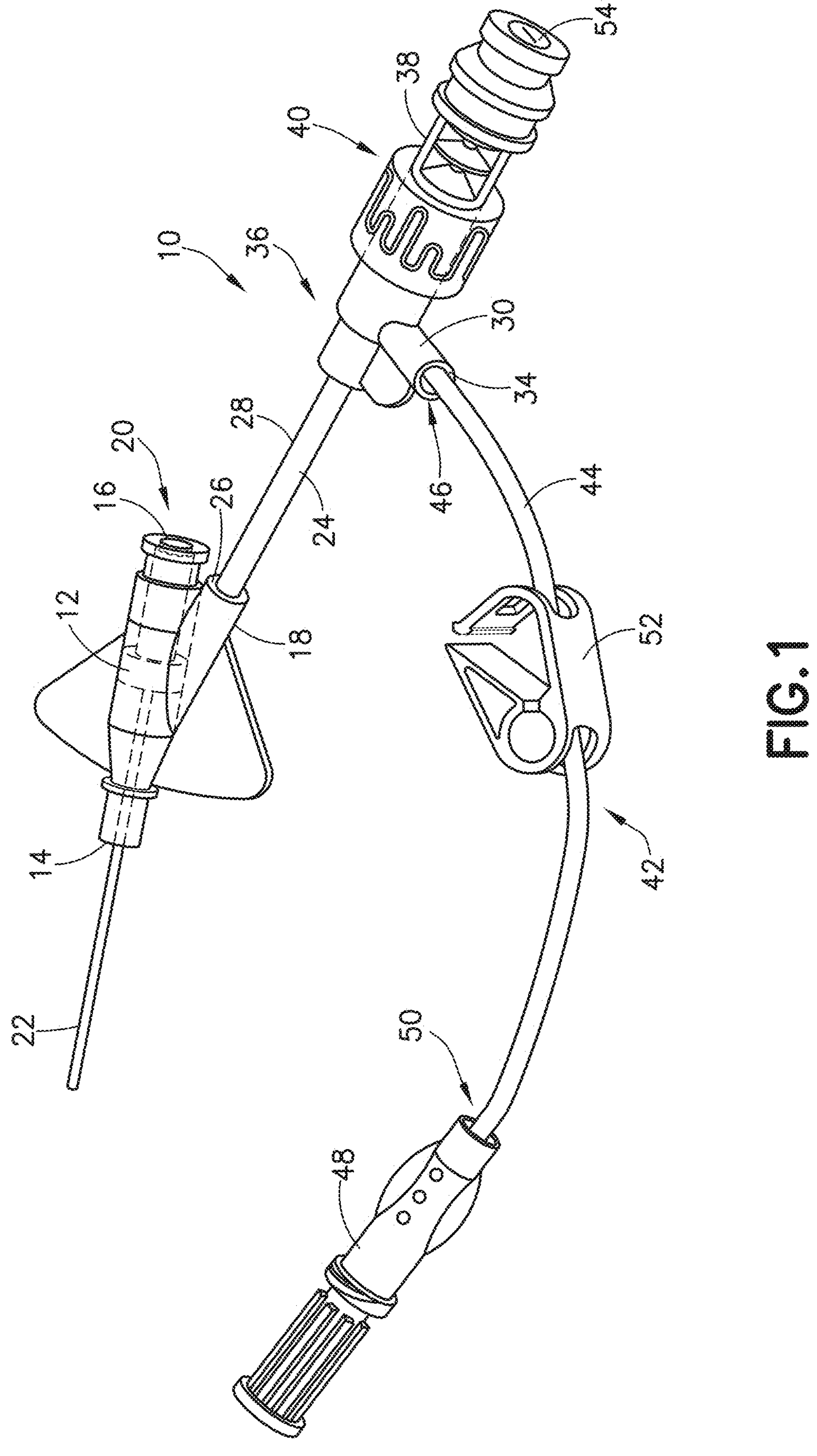
FIG. 1 is a perspective view of a non-limiting embodiment of a prior art catheter assembly useful with disinfecting probes as described herein.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

As used in this specification, the words "proximal" and "distal" refer to the direction closer to and away from, respectively, a user who would place the device into contact with a patient. Thus, for example, the end of a device first touching the body of the patient would be the distal end, while the opposite end of the device being manipulated by the user would be the proximal end of the device.

It should be understood that any numerical range recited herein is intended to include all values and sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

Provided herein are devices and systems for introducing instruments through indwelling catheters, such as peripheral intravenous catheters (PIVCs), peripherally inserted central catheters (PICCs), central venous catheters (CVCs), and midline catheters. While certain catheter assemblies are shown in the accompanying figures and described below, those of skill will appreciate that a disinfecting probe as described herein may be useful in any number of different catheter assembly configurations.

Referring now to FIG. 1, shown is a non-limiting embodiment of a catheter assembly 10 useful with blood draw devices. Catheter assembly 10 may include a catheter adapter 12, which may include a distal end 14 and a proximal end 16. In some embodiments, the catheter adapter 12 may include an additional port 18 that may disposed between the distal end 14 and the proximal end 16 or disposed at the proximal end 16. The first catheter adapter 12 may include a first lumen 20 extending through the distal end 14 and the proximal end 16, and the first lumen 20 may be sealed at proximal end 16 of catheter adapter 12. The catheter assembly 10 may also include a catheter 22 extending from the distal end 14, such as a peripheral intravenous catheter, a midline catheter, or a peripherally-inserted central catheter. Catheter 22 may be formed of any suitable material and may be of any useful length, as known to those of skill in the art.

In some non-limiting embodiments or aspects, the catheter assembly 10 may include a first fluid conduit 24 (or "secondary catheter") extending from the port 18. First fluid conduit 24 may be formed of any suitable material known to those of skill in the art, and may have a distal end 26 and a proximal end 28. The distal end 26 of first fluid conduit 24 is coupled to port 18, while the proximal end 28 of first fluid conduit 24 may be coupled to a connector 30. Connector 30 may be a t-connector (e.g., one side port arranged at a 90 degree angle relative to a longitudinal axis of connector 30), a y-connector (e.g., one side port arranged at a 25, a 60, or a 75 degree angle relative to a longitudinal axis of connector 30), or any other type of connector known in the art. The connector 30 includes a second lumen 32 therethrough, having any number of branches suitable for the type of connector, such as a branch extending between distal and proximal ends 36, 40 of connector 30 and a branch provided to a port 34 of the connector 30.

In some non-limiting embodiments or aspects, catheter assembly 10 may include a needleless access connector 38 coupled to a proximal end 40 of connector 30 and/or an extension set 42 coupled to the port 34 of the connector 30. The extension set 42 may include a second fluid conduit 44 coupled to port 34 at end 46 thereof and a luer connection 48 at opposing end 50, with a clamp 52 provided on second fluid conduit 44 that allows for occlusion thereof. Suitable needleless access connectors 38 can include a split-septum connector or self-healing septum connector, as examples, with a septum 54 shown in FIG. 1 as being provided in the needleless access connector 38. While the non-limiting embodiments of FIGS. 1 and 3 show a needleless access connector 38 arranged at connector 30, those of skill in the art will appreciate that a suitable needleless access connector may also be arranged at luer 48.

As indicated above, it is recognized that during use of the catheter assembly 10, bacteria or other pathogens may enter the fluid path of the catheter assembly 10, i.e., enter the catheter 22, lumen 20 of catheter adapter 12 and/or first fluid conduit 24, which may potentially lead to CRBSIs during a subsequent use. To provide a solution for disinfecting the fluid path, and thereby reduce or prevent the occurrence of CRBSIs, a disinfecting probe is provided for use with the catheter assembly 10.

Figure 2:
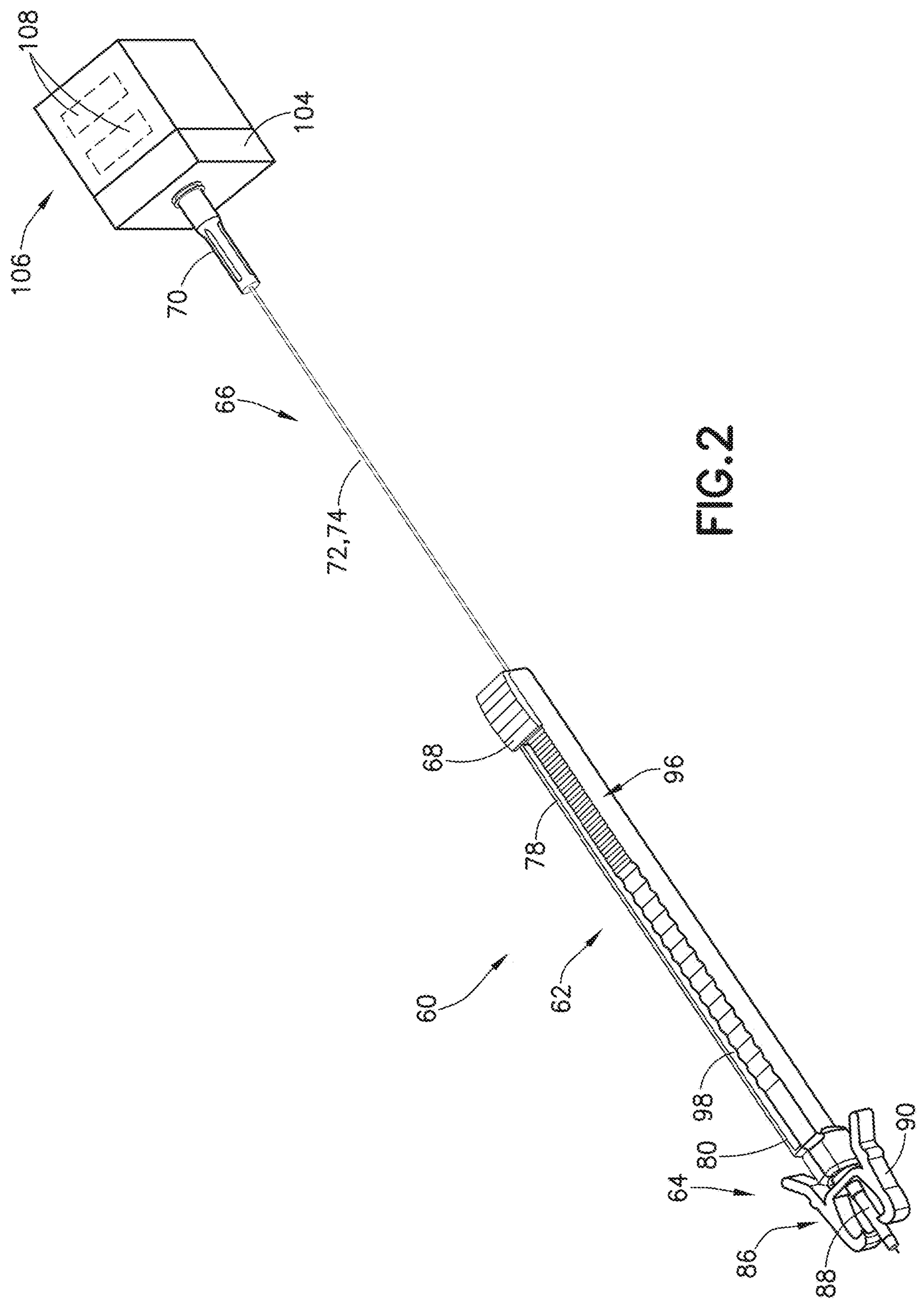
FIG. 2 is a perspective view of a disinfecting probe according to one aspect or embodiment of the disclosure.
Figure 3:
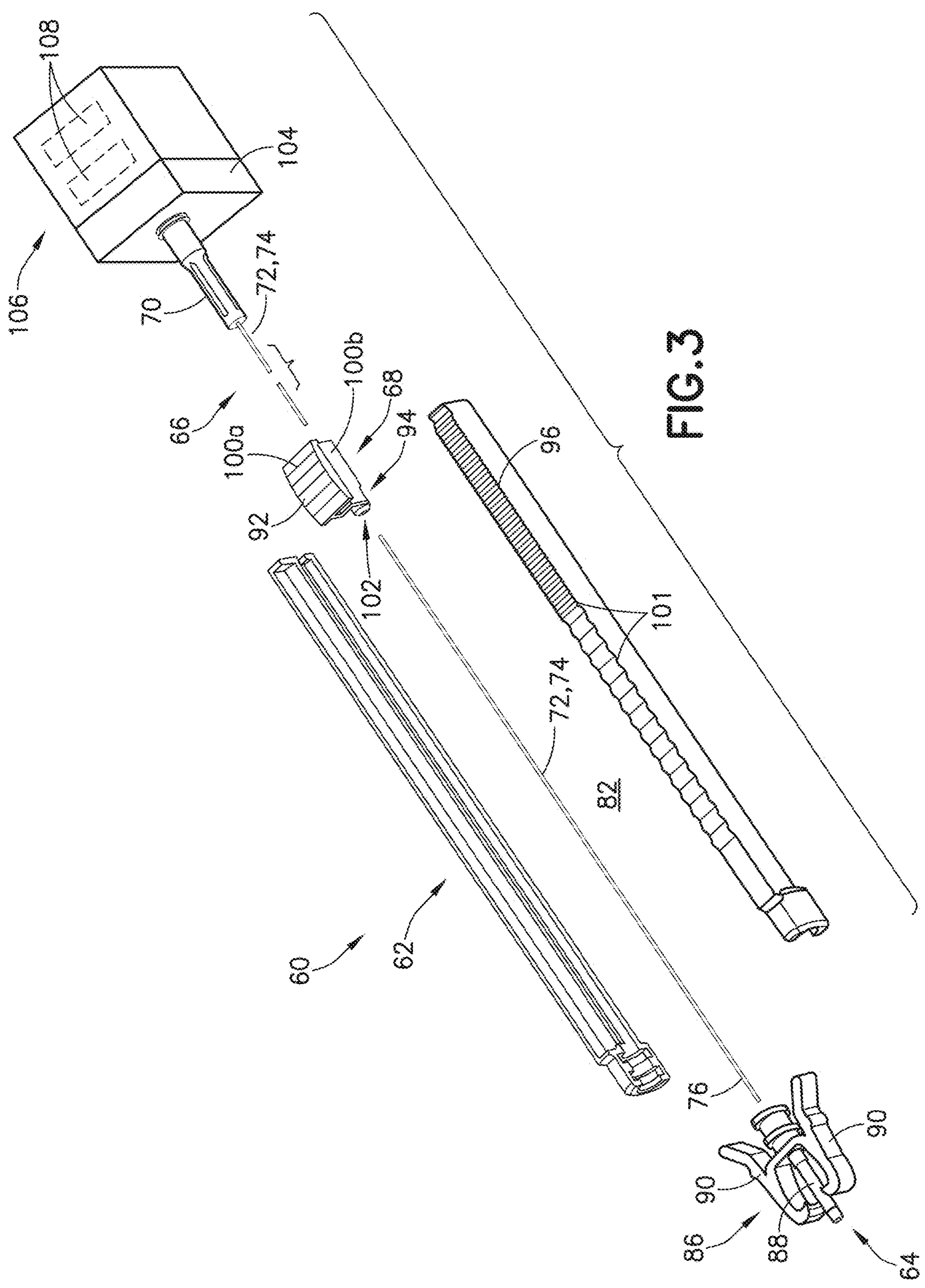
FIG. 3 is an exploded view of the disinfecting probe of FIG. 2.

Turning to FIGS. 2 and 3, shown is a non-limiting embodiment of a disinfecting probe 60 for use with the catheter assembly 10 of FIG. 1. The disinfecting probe 60 includes at least a housing 62, a coupling device 64, a lighting system 66, and an advancement member 68. As will be described in further detail below, at least a portion of the lighting system 66 is moveable within the housing 62 so as to provide for advancement of a portion of the lighting system 66 from inside the housing 62 (i.e., a first position) to outside of the housing 62 (i.e., a second position), such that a distal end thereof may be routed into the catheter assembly 10. Once a portion of the lighting system 66 has been routed into the catheter assembly 10, the lighting system 66 may be controlled to emit disinfecting ultraviolet light that disinfects one or more components of the fluid path in the catheter assembly 10, such as catheter 22, lumen 20 of catheter adapter 12 and/or first fluid conduit 24, as non-limiting examples.

In the embodiment of FIGS. 2 and 3, the lighting system 66 of the disinfecting probe 60 includes an ultraviolet light source 70 and an optical fiber 72 connected thereto that functions to transmit light along a length thereof emitted from the ultraviolet light source 70. The ultraviolet light source 70 may be provided as an ultraviolet lamp configured to emit ultraviolet irradiation of a wavelength suitable for killing or damaging microorganisms (bacteria), so as to provide for sterilization of a tool or component surface with which the UV light contacts. In some embodiments, the ultraviolet light source 70 is thus provided as a UV-C light source that emits ultraviolet irradiation with a wavelength between 200 and 280 nm (and preferably between 250 and 270 nm), although it is recognized that the ultraviolet light source 70 could emit ultraviolet irradiation of other wavelengths able to provide sterilization.

Figures 4, 5:
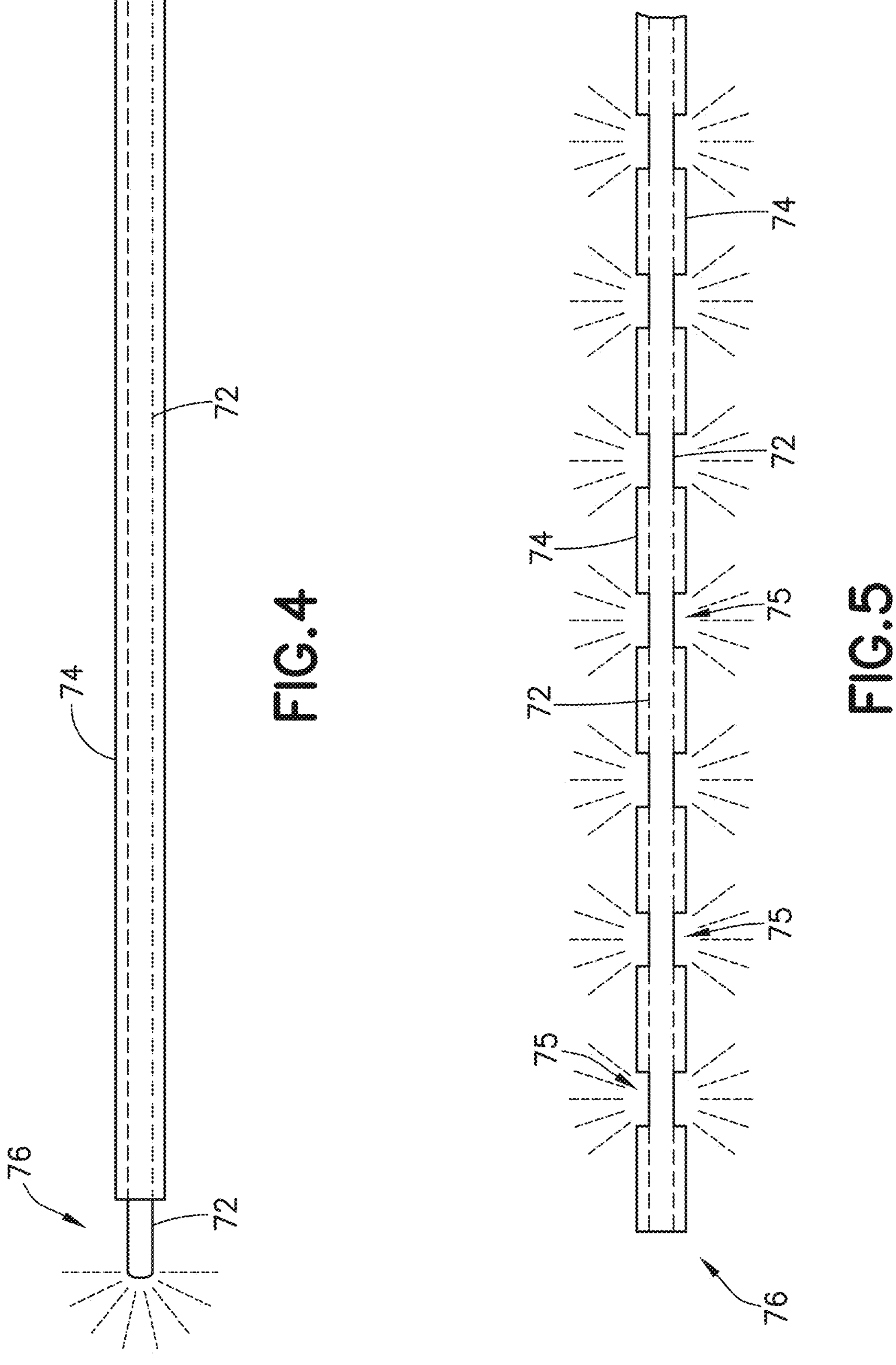
FIG. 4 is a side view of an optical fiber included in the disinfecting probe of FIG. 2, according to one aspect or embodiment of the disclosure.
FIG. 5 is a side view of an optical fiber included in the disinfecting probe of FIG. 2, according to another aspect or embodiment of the disclosure.

The optical fiber 72 is composed of one or more glass fibers of a composition and thickness that allows for the fibers to flex, while also providing for light transmission along a length of the optical fiber 72. In some embodiments, the optical fiber 72 is surrounded by a cladding layer 74 composed of one or more layers of materials having a lower refractive index than that of the glass fibers of optical fiber 72, such that the cladding layer 74 causes light to be confined to the core of the optical fiber 72 by total internal reflection at the boundary between the two. The cladding layer 74 may have one of a number of suitable configurations, according to various embodiments. In the embodiment of FIG. 4, the cladding layer 74 may cover a full length of the optical fiber 72 except for the tip thereof at distal end 76, such that disinfecting ultraviolet light is emitted out from the optical fiber 72 only at the tip. In the embodiment of FIG. 5, the cladding layer 74 the cladding layer 74 covers a length of the optical fiber 72 but includes openings 75 formed therein at locations spaced apart along the length of the optical fiber 72, such that disinfecting ultraviolet light is emitted out from the optical fiber 72 at the locations of the openings 75. Other embodiments may provide the optical fiber 72 without any cladding material 74 applied thereto, and in such embodiments disinfecting ultraviolet light would be emitted out from the optical fiber 72 along an entire length thereof.

The optical fiber 72 is sized to enable introduction thereof into the fluid path (i.e., into a lumen of catheter 22, lumen 20 of catheter adapter 12, and first fluid conduit 24) of catheter assembly 10 and for advancement therethrough, so as to provide for disinfecting of the fluid path. Accordingly, the optical fiber 72 can have an outer diameter (e.g., between a 10-gauge and a 30-gauge) that is smaller than the smallest lumen of the catheter assembly fluid path. The optical fiber 72 can have a length that is sufficient to place a distal end 76 of the optical fiber 72 in a desired position within the fluid path of the catheter assembly 10. Thus, in one embodiment, the optical fiber 72 may have a length sufficient to provide for advancement of the distal end 76 thereof out from the housing 62 and through the catheter assembly 10, catheter adapter 12, and all the way to the distal end of catheter 22.

As shown in FIGS. 2 and 3, the housing 62 of disinfecting probe 60 can be an elongate member having a proximal end

78 and a distal end 80 and defining an inner volume 82. In some embodiments, the housing 62 may be formed of a pair of housing portions 62*a*, 62*b* that are coupled together to define the inner volume 82. The housing 62 may include one or more features or surface finishes on an outer surface thereof that can be arranged to increase the ergonomics of the disinfecting probe 60, which in some instances can allow a user to manipulate the disinfecting probe 60 with one hand (i.e., single-handed use). Additionally, the proximal end 78 of the housing 62 can include an opening or port 84 configured to receive a portion of the optical fiber 72 (i.e., the portion of the optical fiber 72 extending out from ultraviolet light source 70) and provide for advancement and retraction of the optical fiber 72 through the port 84.

The coupling device 64 of disinfecting probe 60 is provided at the distal end 80 of the housing 62, with the coupling device 64 providing for reversible coupling of the disinfecting probe 60 to catheter assembly 10, such as via needleless access connector 38 as shown in FIG. 1. In some embodiments, the coupling device 64 is configured as a lock 86 that includes a blunted cannula 88 and locking arms 90 for coupling to the needleless access connector 38 of catheter assembly 10, with the blunted cannula 88 and locking arms 90 forming three points of contact therewith. However, those of skill will appreciate that any connection or coupling, for example a luer, can be used, so long as the distal end 76 of optical fiber 72 may pass through the coupling device 64 to access catheter assembly 10.

The advancement member 68 of disinfecting probe 60 includes a first portion 92 and a second portion 94. The first portion 92 is movably disposed along an upper surface 96 of the housing 62 and the second portion 94 is movably disposed within the inner volume 82 of the housing 62. The arrangement of the advancement member 68 and the housing 62 is such that a connecting portion (not shown) of the advancement member 68 that joins the first and second portions 92, 94 is seated within a slot 98 formed in the upper surface 96 of the housing 62—the slot 98 generally extending between the proximal and distal ends 78, 80 of the housing 62. As the first and second portions 92, 94 are joined together, movement of the first portion 92 along the upper surface 96 of the housing 62 results in a corresponding movement of the second portion 94 within the inner volume 82.

As shown in FIGS. 2 and 3, the first portion 92 of the advancement member 68 may be configured as a tab or tab having a contact surface 100*a* engageable by a user and an underside 100*b* that is in contact with the outer surface 96 of the housing 62. In such embodiments, the upper surface 96 of the housing 62 can include a track 101, for example, a set of ribs, ridges, bumps, grooves, and/or the like along which the underside 100*b* of tab or protrusion advances when the advancement member 68 is engaged by a user. In this manner, a user can engage the first portion 92 of the advancement member 68 and can move the advancement member 68 relative to the housing 62.

As further shown in FIG. 3, the second portion 94 includes an opening 102 extending therethrough that is configured to grip or retain a portion of the optical fiber 72. Due to a portion of the optical fiber 72 being retained within the opening 102 of second portion, 94, movement of the advancement member 68 relative to housing 62 causes a corresponding movement of the optical fiber 72 relative to the housing 62. In this manner, the distal end 76 of the optical fiber 72 can be selectively moved out of or back into the inner volume 82 of the housing 62 as desired, such as advancing the distal end 76 of the optical fiber 72 out of the housing 62 when the disinfecting probe 60 has been coupled to the catheter assembly 10 and a disinfecting procedure is to be performed.

Figure 6:
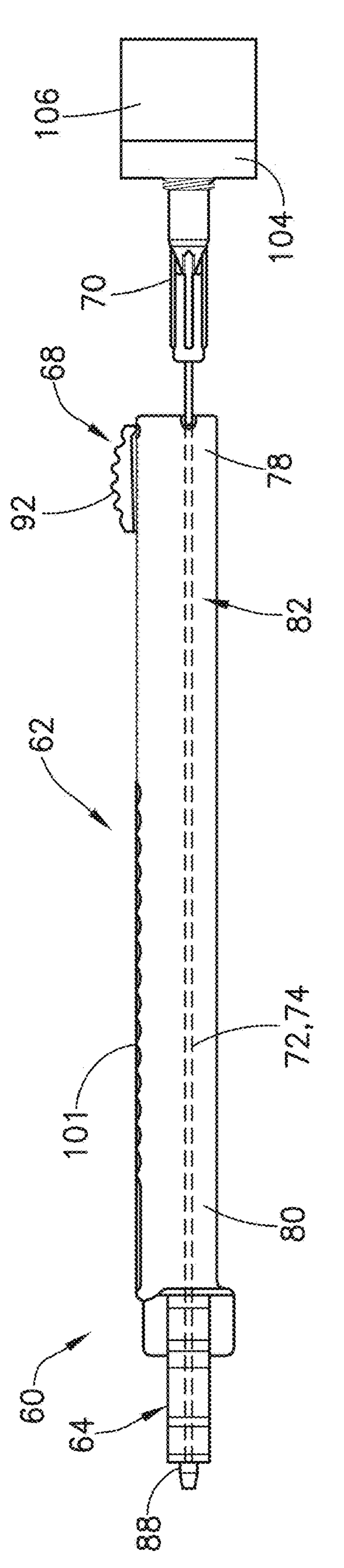
FIG. 6 is a side view of the disinfecting probe of FIG. 2 in a retracted position.
Figure 7:
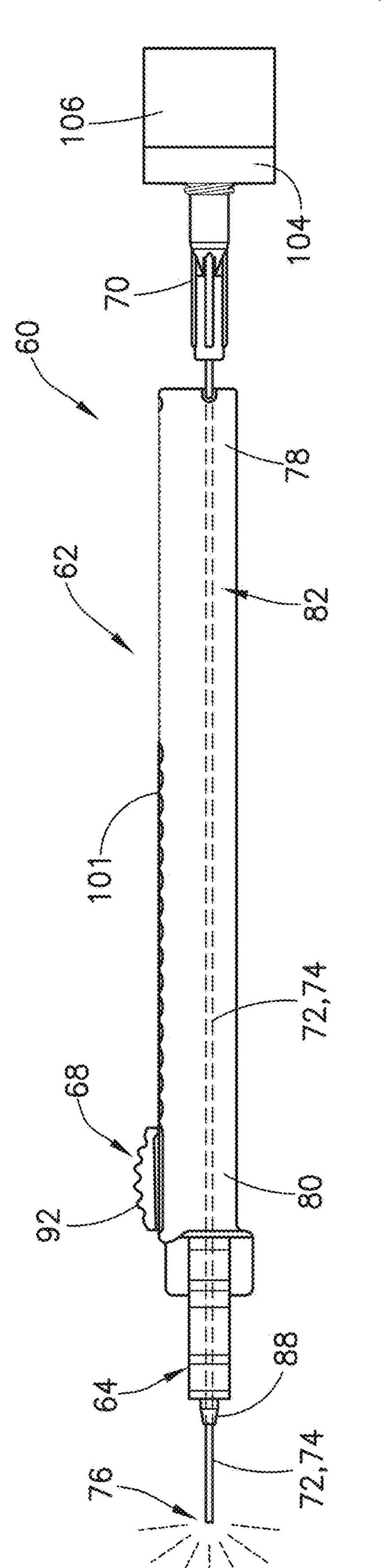
FIG. 7 is a side view of the disinfecting probe of FIG. 2 in an extended position.
Figure 8:
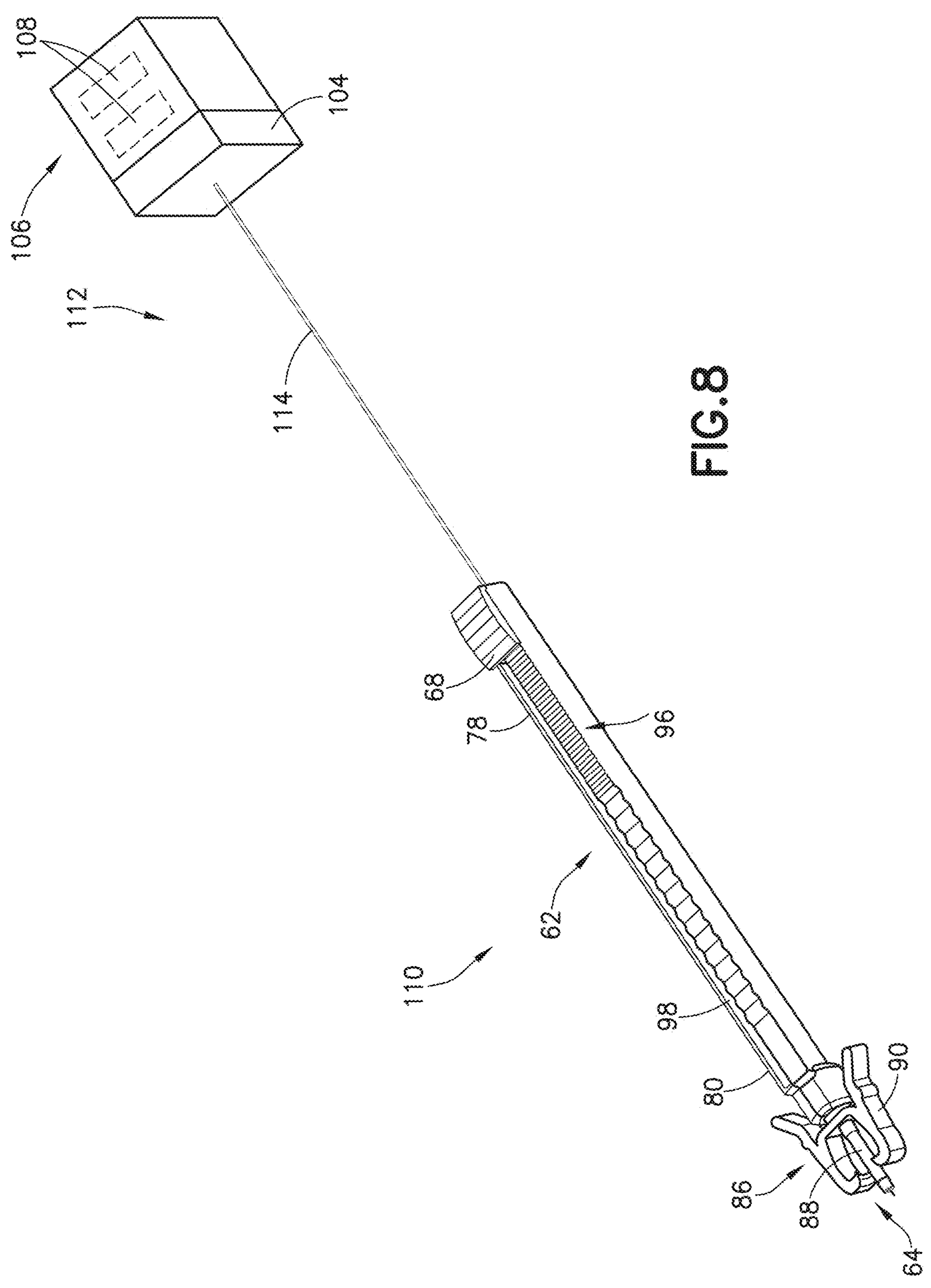
FIG. 8 is a perspective view of a disinfecting probe according to another aspect or embodiment of the disclosure.
Figure 9:
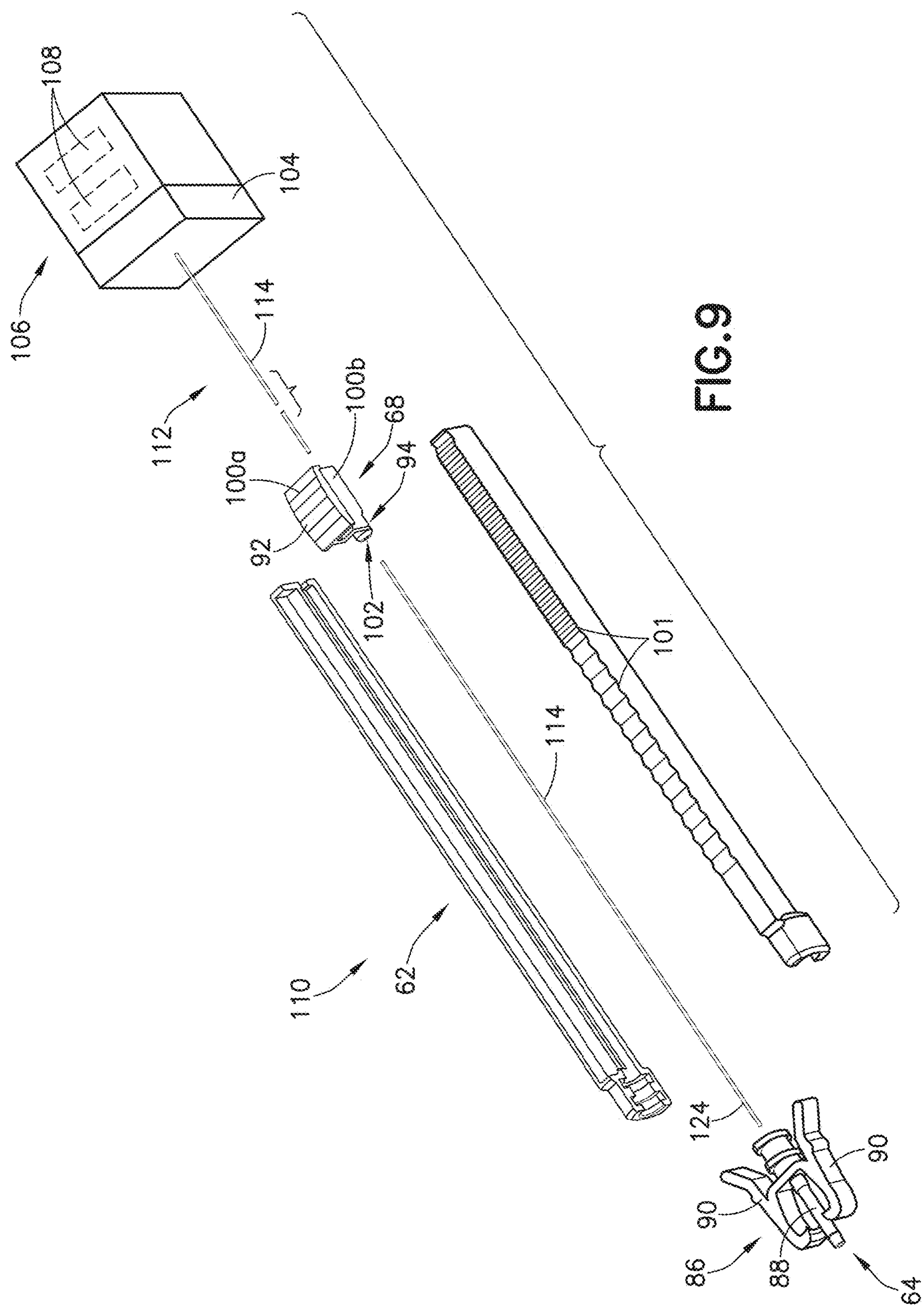
FIG. 9 is an exploded view of the disinfecting probe of FIG. 8.

FIGS. 6 and 7 illustrate operation of the disinfecting probe 60 with the optical fiber 72 moved between a first position and a second position. More specifically, at least the distal end 76 of the optical fiber is disposed within the inner volume 82 when the optical fiber 72 is in the first position (FIG. 6), and at least a portion of the optical fiber 72 extends out from the distal end of the housing 62 and through coupling device 64 (and into the catheter assembly 10 of FIG. 1) when the optical fiber 72 is in the second position (FIG. 7). The configuration of the disinfecting probe 60, specifically the length of optical fiber 72 that may be extended out past the housing 62 and coupling device 64, may be determined based on the construction of the catheter assembly 10 with which it is to be used, including the length of the fluid path therein through which the optical fiber 72 is to be advanced.

Operation of the disinfecting probe 60 will now be described in more detail according to embodiments of the disclosure. In an initial step of operating the disinfecting probe 60, the disinfecting probe 60 is first connected to the catheter assembly 10 by inserting the blunted cannula 88 into the needleless access connector 38 and securing the locking arms 90 in place. Next steps of operation include powering on the lighting system 66 (via a battery 104 or via a supplied line power) and advancing the optical fiber 72 through the fluid path of the catheter assembly 10, with it recognized that the order of these steps can vary depending on the construction of the lighting system 66.

In an embodiment where the lighting system 66 is configured with the optical fiber 72 having cladding 74 applied along an entire length thereof except for the tip at distal end 76 (FIG. 4), the ultraviolet light source 70 is first powered on, such that disinfecting ultraviolet light is emitted out from the ultraviolet light source 70 and transmitted through optical fiber 72 to be emitted from the tip. The optical fiber 72 is then subsequently advanced through portions of the fluid path of the catheter assembly 10 (via actuation of advancement member 68, as previously described), with areas of the fluid path being disinfected as the tip of the optical fiber 72 passes adjacent therethrough (i.e., the space surrounding the tip is disinfected) due to disinfecting ultraviolet light being emitted onto those areas. In one embodiment, advancement of the optical fiber 72 may be continued until the tip of the optical fiber 72 reaches a desired area of catheter 22.

In an embodiment where the lighting system 66 is configured with the cladding 74 having openings 75 formed therein that are spaced along a length of the optical fiber 72 (FIG. 5), the optical fiber 72 is first advanced through those portions of the fluid path of the catheter assembly 10 that are to be disinfected (again, via actuation of advancement member 68 as previously described). In one embodiment, advancement of the optical fiber 72 may be continued until the tip of the optical fiber 72 reaches a desired area of catheter 22. Subsequent to advancement of the optical fiber 72 into the fluid path of the catheter assembly 10 as desired, the ultraviolet light source 70 is then powered on, such that disinfecting ultraviolet light is emitted out from the ultraviolet light source 70 and transmitted through optical fiber 72 to be emitted through the openings 75 provided in the cladding. The optical fiber 72 may be kept in place for a pre-determined amount of time with the disinfecting ultraviolet light being emitted out from the optical fiber 72, with it recognized that the openings 75 are spaced apart in a manner that allows all areas of the catheter assembly fluid path to be exposed to disinfecting ultraviolet light when the optical fiber 72 is advanced into place.

It is recognized that operation of the lighting system 66 may be provided via a control system 106 provided therein. According to embodiments, the control system 106 may include a plurality of control related components 108—such as one or more of an On-Off switch, a timer, and a communications device (e.g., WiFi or Bluetooth transmitter/receiver, or USB port), as examples—that enable an operator to selectively control operation of the lighting system 66, including a duration and/or intensity of emission of disinfecting ultrasonic light provided therefrom. Via such selective control of the disinfecting probe 60, proper disinfecting of the catheter assembly fluid path can be ensured.

Referring now to FIGS. 8-12, a disinfecting probe 110 is shown according to another embodiment. The construction of the disinfecting probe 110 may align closely with that of the disinfecting probe 60 of FIGS. 2-7, and thus common numbering is used here to identify identical components in the disinfecting probe 110, but a lighting system 112 included in the disinfecting probe 110 differs from that of lighting system 66. Specifically, lighting system 112 includes a lighting element 114 formed of a guide wire 116 and a light strip 118, with the light strip 118 including a plurality of ultraviolet light emitting diodes (LEDs) 120 that are configured to emit the disinfecting ultraviolet light.

Figure 10:
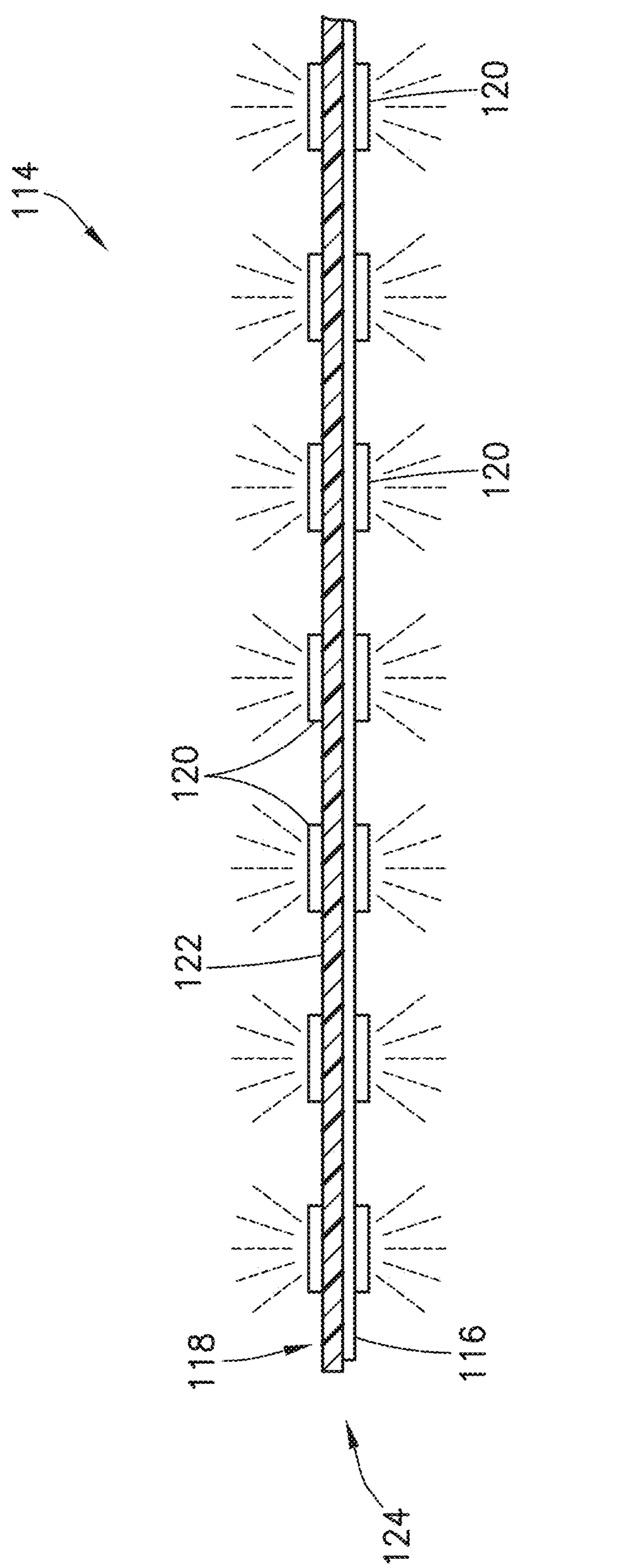
FIG. 10 is a side view of a lighting element included in the disinfecting probe of FIG. 8, according to one aspect or embodiment of the disclosure.

As best shown in FIG. 10, the guide wire 116 and light strip 118 of lighting element 114 are coupled to together to provide a semi-rigid but flexible structure capable of being advanced outside the housing 62 of the disinfecting probe 110 and into a connected catheter assembly. The guide wire 116 may be formed of a suitable material (e.g., stainless steel or nitinol, for example) and structured as a solid or coiled/braided wire that offers a large amount of flexibility, pushability and kink resistance. Additionally, the guide wire 116 may be covered with a polymeric and/or hydrophilic coating to increase lubricity and reduce friction during deployment. The light strip 118 is coupled to guide wire 116 and is formed from a plurality of ultraviolet LEDs 120 that are mounted on a flexible substrate 122. The flexible substrate 122 may be formed as a thin-film integrated circuit (IC) substrate 122 that includes wiring therein configured to provide power and control connections to the ultraviolet LEDs 120 mounted thereon. The ultraviolet LEDs 120 are spaced apart equally, at regular intervals on the substrate 122, such that disinfecting ultraviolet light emitted therefrom during use provides complete and consistent coverage along a length of the light strip 118. In the illustrated embodiment, the ultraviolet LEDs 120 are positioned on opposing side of the substrate 122 to enable emission of disinfecting ultraviolet light across a broader range, but it is recognized that the ultraviolet LEDs 120 could only be provided on the top or bottom of the substrate 122, or that the ultraviolet LEDs 120 could be provided as cylindrical elements that encircle the substrate 122, according to other embodiments.

Similar to arrangement of the optical fiber 72 in the disinfecting probe 60 as described above in the embodiment of FIGS. 2-7, a portion of the lighting element 114 is retained within the second portion 94 of advancement member 68 (i.e., in opening 102 thereof), such that movement of the advancement member 68 relative to housing 62 causes a corresponding movement of the lighting element 114 relative to the housing 62. In this manner, a distal end 124 of the lighting element 114 can be selectively moved out of or back into the inner volume 82 of the housing 62 as desired, such as advancing the distal end 124 of the lighting element 114 out of the housing 62 when the disinfecting probe 60 has been coupled to the catheter assembly 10 and a disinfecting procedure is to be performed.

Figure 11:
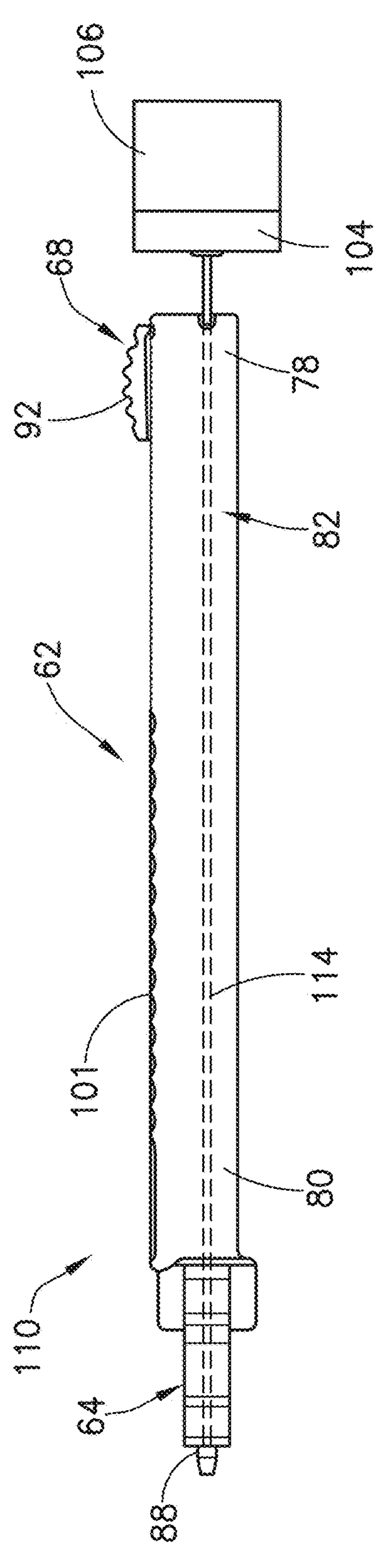
FIG. 11 is a side view of the disinfecting probe of FIG. 8 in a retracted position.
Figure 12:
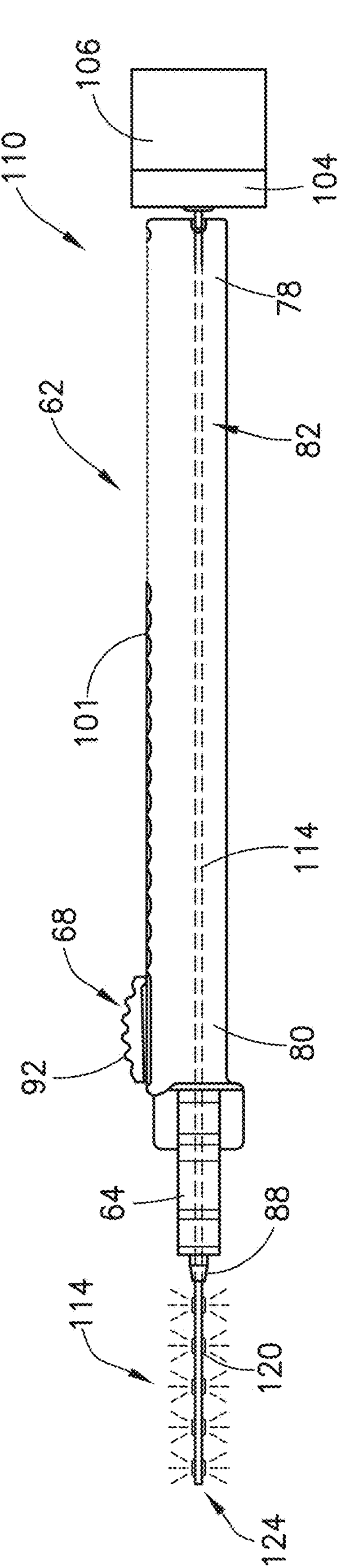
FIG. 12 is a side view of the disinfecting probe of FIG. 8 in an extended position.

FIGS. 11 and 12 illustrate operation of the disinfecting probe 110 with the lighting element 114 moved between a first position and a second position. More specifically, at least the distal end 124 of the lighting element 114 is disposed within the inner volume 82 when the lighting element 114 is in the first position (FIG. 11), and at least a portion of the lighting element 114 extends out from the distal end 80 of the housing 62 and through coupling device 64 (and into the catheter assembly 10 of FIG. 1) when the lighting element 114 is in the second position (FIG. 12). The configuration of the disinfecting probe 110, specifically the length of lighting element 114 that may be extended out past the housing 62 and coupling device 64, may be determined based on the construction of the catheter assembly 10 with which it is to be used, including the length of the fluid path therein through which the lighting element 114 is to be advanced.

Operation of the disinfecting probe 110 will now be described in more detail according to embodiments of the disclosure. In an initial step of operating the disinfecting probe 110, the disinfecting probe 110 is first connected to the catheter assembly 10 by inserting the blunted cannula 88 into the needleless access connector 38 and securing the locking arms 90 in place. The lighting element 114 is then advanced through those portions of the fluid path of the catheter assembly 10 that are to be disinfected (again, via actuation of advancement member 68 as previously described). In one embodiment, advancement of the lighting element 114 may be continued until the tip of the lighting element 114 reaches a desired area of catheter 22. Subsequent to advancement of the lighting element 114 into the fluid path of the catheter assembly 10 as desired, the ultraviolet LEDs 120 are then powered on, such as via a battery 104 or a supplied line power, such that disinfecting ultraviolet light is emitted out from the ultraviolet LEDs 120 of lighting element 114. The lighting element 114 may be kept in place for a pre-determined amount of time while the disinfecting ultraviolet light is emitted out from the ultraviolet LEDs 120, with it recognized that the ultraviolet LEDs 120 are spaced apart in a manner that allows all areas of the catheter assembly fluid path to be exposed to disinfecting ultraviolet light when the lighting element 114 is advanced into place.

It is recognized that operation of the lighting element 114 may be provided via a control system 106 included in lighting system 112. According to embodiments, the control system 106 may include a plurality of control related components 108—including one or more of an On-Off switch, a timer, and a communications device (e.g., WiFi or Bluetooth transmitter/receiver, or USB port), as examples—that enable an operator to selectively control operation of the lighting element 114, including a duration and/or intensity of emission of disinfecting ultrasonic light provided therefrom. Via such selective control of the disinfecting probe 110, proper disinfecting of the catheter assembly fluid path can be ensured.

Figure 13:
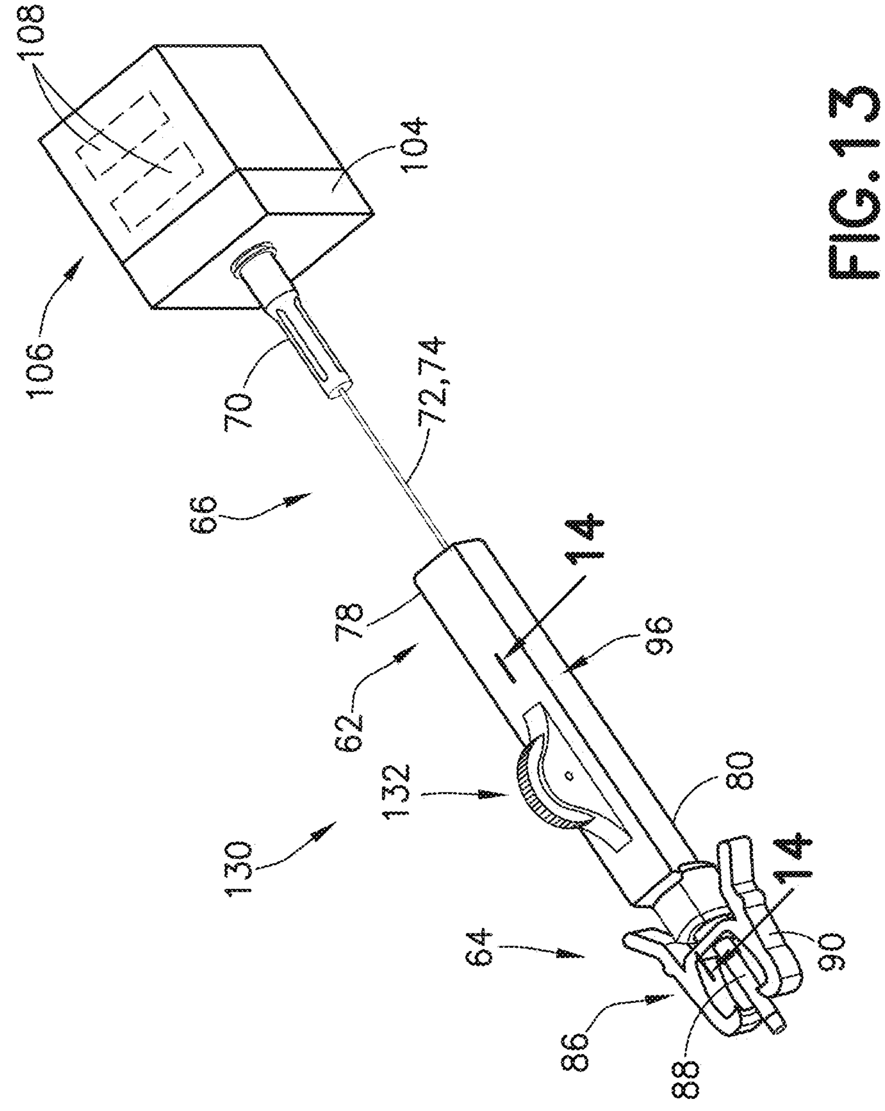
FIG. 13 is a perspective view of a disinfecting probe according to another aspect or embodiment of the disclosure.
Figure 14:
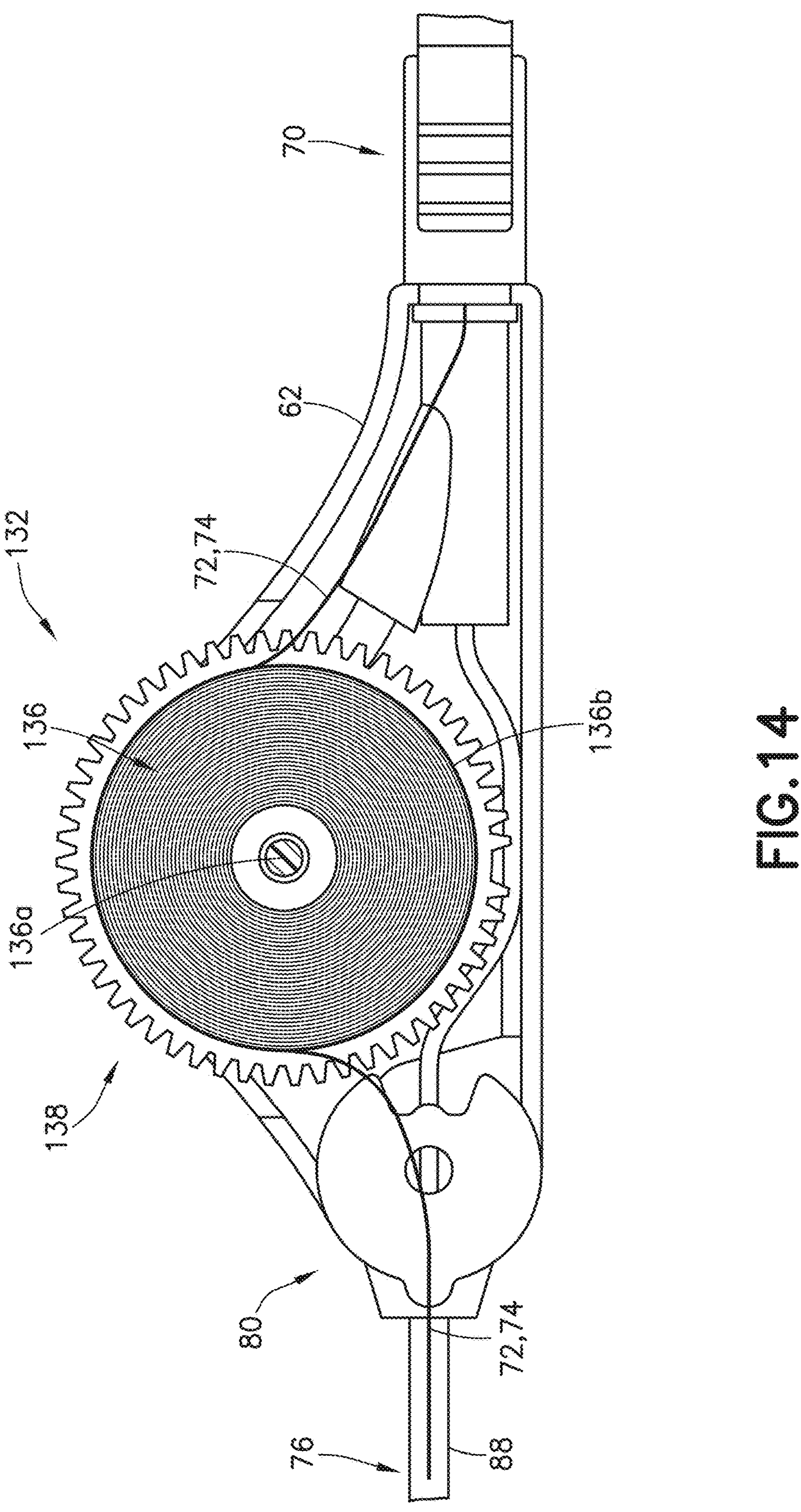
FIG. 14 is a side cross-section view of a portion of the disinfecting probe of FIG. 13, taken along line 14-14, and showing a wheel member thereof, according to an aspect or embodiment of the disclosure.

Referring now to FIGS. 13 and 14, a disinfecting probe 130 is shown according to another embodiment that may be advantageously used for disinfecting the internal fluid path of a long catheter, such as a PICC or a CVC. In the disinfecting probe 130, a wheel member 132 is provided on the housing 62 at the distal end 80 thereof to act as an advancement member for the probe. The wheel member 132 replaces the advancement member 68 included in the disinfecting probes 60, 110 shown and described previously, and is configured to provide for advancement and retraction of a lighting component in the disinfecting probe 130. While wheel member 132 is described here as advancing/retracting optical fiber 72 (and cladding 74), it is recognized that the wheel member could also interact with lighting element 114 (guide wire 116 and light strip 118), according to other embodiments. In operation of the disinfecting probe 130, an operator actuates (e.g., rotates) the wheel member 132, which in turn causes a linear advancement or retraction of the optical fiber 72, depending on the direction of rotation of the wheel member 132.

As shown in FIG. 14, wheel member 132 is positioned in a compartment 134 formed in housing 62. Wheel member 132 includes a spool 136 and an advancement wheel 138. The spool 136 includes an axle 136*a* that maintains spool 136 within compartment 134 and allows the spool 136 to rotate. The spool 136 also includes a spool drum 136*b* around which the optical fiber 72 is wound. The advancement wheel 138 extends upwardly from compartment 134, so as to be engageable by an operator. An operator can directly rotate advancement wheel 138 by applying a force thereto, with the advancement wheel 138 rotatable in a forward or reverse direction.

In operation of the disinfecting probe 130, rotation of the advancement wheel 138 in the forward direction (i.e., toward the distal end 80 of the housing 62) causes the optical fiber 72 to advance toward the distal end 80 of the housing 62, such that the distal end 76 of the optical fiber 72 may be extended out from housing 62 and blunted cannula 88 and into a catheter assembly. Conversely, when the advancement wheel 138 is rotated in the reverse direction (i.e., toward the proximal end 78 of the housing 62), the optical fiber 72 is caused to retract back toward the proximal end 78 of the housing 62, such that the distal end 76 of the optical fiber 72 may be drawn back into the housing 62.

Beneficially, embodiments of the present disclosure thus provide a disinfecting probe useable with a catheter assembly to disinfect the internal fluid path of the indwelling catheter of the catheter assembly. The distal end of the disinfecting probe may be advanced into the catheter assembly and disinfecting ultraviolet light (UV-C) emitted therefrom to disinfect the fluid path, to sterilize the fluid path and thereby reduce the likelihood of CRBSIs.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A catheter system, comprising:

an intravenous catheter assembly comprising:

a catheter comprising a distal end and a proximal end, the catheter defining a lumen extending between the distal end and the proximal end; and an access connector configured to provide access to the lumen of the catheter; and a disinfecting probe coupleable to the access connector, the disinfecting probe comprising:

a housing having a proximal end and a distal end;

a lighting system disposed at least partially within the housing and configured to emit a disinfecting ultraviolet light, the lighting system comprising:

an optical fiber extending distally through at least a portion of the housing and configured to transmit the disinfecting ultraviolet light along a length of the optical fiber; and an advancement member configured to selectively move the optical fiber from a first position to a second position, wherein:

a distal end of the optical fiber is disposed within the housing when the optical fiber is in the first position, the distal end of the optical fiber extends beyond the distal end of the housing and into the catheter when the optical fiber is in the second position, responsive to movement of the advancement member with respect to the housing, and the disinfecting ultraviolet light disinfects the lumen of the catheter upon being advanced therein by the advancement member.

2. The system of claim 1, wherein the access connector comprises a needleless access connector, and wherein the disinfecting probe comprises a blunt cannula at the distal end of the housing that is reversibly coupleable to the needleless access connector; and wherein the advancement member is configured to advance a portion of the lighting system through the blunt cannula and the needleless access connector, into the lumen of the catheter.

3. The system of claim 1, wherein the lighting system comprises:

an ultraviolet light source positioned adjacent the proximal end of the housing and configured to emit the disinfecting ultraviolet light; wherein:

the optical fiber extends out distally from the ultraviolet light source.

4. The system of claim 3, wherein the lighting system comprises a cladding covering a portion of the optical fiber and that is configured to block transmission of the disinfecting ultraviolet light.

5. The system of claim 1, wherein the cladding covers a full length of the optical fiber except for a tip at the distal end of the optical fiber, such that the disinfecting ultraviolet light is emitted only from the tip.

6. The system of claim 4, wherein the cladding covers a length of the optical fiber and includes openings formed therein at locations spaced apart along the length of the optical fiber, such that the disinfecting ultraviolet light is emitted from the optical fiber only at the locations.

7. The system of claim 1, wherein the lighting system comprises:

a guide wire; and a light strip mounted on the guide wire, the light strip comprising a plurality of ultraviolet light emitting diodes (LEDs) configured to emit the disinfecting ultraviolet light;

wherein the advancement member is configured to advance a portion of the guide wire and the light strip beyond the distal end of the housing.

8. The system of claim 7, wherein the plurality of ultraviolet LEDs are equally spaced along a length of the light strip.

9. The system of claim 1, wherein the advancement member is configured to move along an outer surface of the housing, and wherein the advancement member engages the lighting system to advance the portion of the lighting system beyond the distal end of the housing and into the catheter.

10. The system of claim 1, wherein the lighting system comprises a control system configured to selectively control emission of the disinfecting ultraviolet light, the control system comprising one or more of an on/off switch, a timer, and a communication device.

11. The system of claim 1, wherein the lighting system is configured to emit UV-C light.

12. The system of claim 1, wherein the advancement member comprises a wheel member positioned on the housing and rotatable relative to the housing, wherein the wheel member is operably coupled to a lighting component of the lighting system, to advance and retract the lighting component out of and back into the housing when the wheel member is rotated.

13. A disinfecting probe for disinfecting a catheter of an intravenous catheter assembly, the disinfecting probe comprising:

a housing having a proximal end and a distal end;

a lighting system disposed at least partially within the housing and configured to emit a disinfecting ultraviolet light, the lighting system comprising:

an optical fiber extending distally through at least a portion of the housing and configured to transmit the disinfecting ultraviolet light along a length of the optical fiber; and an advancement member configured to selectively move the optical fiber from a first position to a second position, wherein:

a distal end of the optical fiber is disposed within the housing when the optical fiber is in the first position, the distal end of the optical fiber extends beyond the distal end of the housing and into the catheter when the optical fiber is in the second position, responsive to movement of the advancement member with respect to the housing, and the disinfecting ultraviolet light disinfects a lumen of the catheter upon being advanced therein by the advancement member.

14. The disinfecting probe of claim 13, further comprising a blunt cannula positioned at the distal end of the housing, the blunt cannula reversibly coupleable to a needleless access connector of the intravenous catheter assembly;

wherein the advancement member is configured to advance a portion of the lighting system through the blunt cannula and the needleless access connector, into the lumen of the catheter.

15. The disinfecting probe of claim 13, wherein the lighting system comprises:

an ultraviolet light source positioned adjacent the proximal end of the housing and configured to emit the disinfecting ultraviolet light, wherein:

the optical fiber extends out distally from the ultraviolet light source.

16. The disinfecting probe of claim 15, wherein the lighting system comprises a cladding covering a portion of the optical fiber and that is configured to block transmission of the disinfecting ultraviolet light.

17. The disinfecting probe of claim 16, wherein the cladding covers a full length of the optical fiber except for a tip at the distal end of the optical fiber, such that the disinfecting ultraviolet light is emitted only from the tip.

18. The disinfecting probe of claim 16, wherein the cladding covers a length of the optical fiber and includes openings formed therein at locations spaced apart along the length of the optical fiber, such that the disinfecting ultraviolet light is emitted from the optical fiber only at the locations.

19. The disinfecting probe of claim 13, wherein the lighting system comprises:

a guide wire; and a light strip mounted on the guide wire, the light strip comprising a plurality of ultraviolet light emitting diodes (LEDs) configured to emit the disinfecting ultraviolet light;

wherein the advancement member is configured to advance a portion of the guide wire and the light strip beyond the distal end of the housing.

20. The disinfecting probe of claim 19, wherein the plurality of ultraviolet LEDs are equally spaced along a length of the light strip.

21. The disinfecting probe of claim 13, wherein the advancement member is configured to move along an outer surface of the housing, and wherein the advancement member engages the lighting system to advance a portion of the lighting system beyond the distal end of the housing and into the catheter.

* * * * *